United States Patent [19]
Bartels-Keith et al.
[11] 4,365,085
[45] Dec. 21, 1982

[54] BICYCLIC REDUCTONE DEVELOPING AGENTS

[75] Inventors: James R. Bartels-Keith, Lexington; Eva R. Karger, Arlington, both of Mass.

[73] Assignee: Polaroid Corporation, Cambridge, Mass.

[21] Appl. No.: 9,745

[22] Filed: Feb. 5, 1979

Related U.S. Application Data

[62] Division of Ser. No. 881,544, Feb. 27, 1978, Pat. No. 4,154,611.

[51] Int. Cl.[3] .................... C07C 97/07; C07C 102/06; C07C 103/44; C07C 103/46; C07C 119/00; C07C 119/06

[52] U.S. Cl. ................................ 560/251; 260/404.5; 260/545 R; 430/218; 430/234; 430/239; 430/249; 430/419; 430/442; 430/456; 450/484; 546/186; 560/107; 560/118; 560/252; 562/500; 564/152; 564/153; 564/217; 564/460

[58] Field of Search ........................ 560/251, 252, 118; 562/500; 564/152, 153, 217, 460; 260/404.5, 545 R

[56] References Cited

U.S. PATENT DOCUMENTS

| | | | |
|---|---|---|---|
| 2,691,589 | 10/1954 | Henn et al. | 95/88 |
| 3,615,440 | 10/1971 | Bloom et al. | 96/29 |
| 3,664,835 | 5/1972 | Youngquist | 96/3 |
| 3,672,896 | 6/1972 | Gabrielsen et al. | 99/66 HD |
| 3,690,872 | 9/1972 | Gabrielsen et al. | 99/66 HD |
| 3,816,137 | 6/1974 | Gabrielsen et al. | 96/76 |

OTHER PUBLICATIONS

Meisenheimer, Justus Liebigs Ann. Chem., 323, 205, 1902.

Kohashi et al., Chem. Pharm. Bull. (Tokyo), 18, 2151, 1970; 19, 213, 1971.

Kabeya et al., Chem. Pharm. B (Tokyo) 19,645 (1971).

Straus et al., J. Org. Chem., 35, 383 (1970); 36, 856 (1971).

*Primary Examiner*—Vivian Garner
*Attorney, Agent, or Firm*—Sybil A. Campbell

[57] ABSTRACT

The present invention relates to novel bicyclic compounds useful as photographic silver halide developing agents, to the preparation of these compounds and to photographic products, processes and compositions employing the same. The subject compounds may be represented by the formula

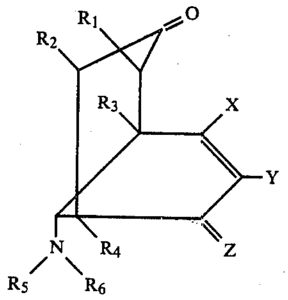

wherein $R_1$ and $R_2$, the same or different, each represents hydrogen, a hydrocarbon moiety, preferably an alkyl group, —COOH or —$COOR^1$ wherein $R^1$ is an alkyl group; $R_3$ and $R_4$, the same or different, each represent hydrogen or an alkyl group, $R_5$ represents hydrogen or —$COR^2$ wherein $R^2$ is an alkyl group; $R_6$ represents hydrogen when $R_5$ is hydrogen and represents hydrogen or —$OCOR^3$ wherein $R^3$ is an alkyl group the same as $R^2$ when $R_5$ represents —$COR^2$; X represents —OH, —$NH_2$ or —$NHCOR^4$ wherein $R^4$ represents an alkyl group the same as $R^2$; Y represents —OH or —$OCOR^5$ wherein $R^5$ represents an alkyl group the same as $R^2$; and Z represents =O or =$NCOR^6$ wherein $R^6$ is an alkyl group the same as $R^2$.

15 Claims, No Drawings

BICYCLIC REDUCTONE DEVELOPING AGENTS

This is a division of application Ser. No. 881,544, filed Feb. 27, 1978, now U.S. Pat. No. 4,154,611.

BACKGROUND OF THE INVENTION

1. Field of the Invention

This invention relates to photography and to novel chemical compounds useful therein. More particularly, it relates to novel chemical compounds useful in the development of photosensitive silver halide materials and to photographic products, processes and compositions employing the same.

2. Description of the Prior Art

It has been known for quite some time that Meisenheimer complexes are formed from sym-trinitrobenzene (TNB), tertiary amines, and certain ketones; see, for example, J. Meisenheimer, Justus Liebigs Ann. Chem., 323, 205 (1902). More recently it has been shown that a Meisenheimer type, a bicyclic type and a tetracyclic type compound were formed as the main coloring matters of the reaction of acetone with 1,3,5-trinitrobenzene in an alkaline medium as reported by K. Kohashi et al, Chem. Pharm. Bull. (Tokyo), 18, 2151 (1970) and K. Kohashi et al, ibid., 19, 213 (1971) and T. Kabeya et al, ibid., 19, 645 (1971). Of interest in the latter reports was the discovery of the formation of a bicyclic compound in the reaction between acetone, picric acid and piperidine to yield the bicyclic nitronate salt. The reaction of other acyclic ketones with electron-deficient aromatics in the presence of secondary amines has been shown to yield similarly interesting bicyclic compounds; see, for example, M. J. Strauss et al, J. Org. Chem., 36, 856 (1971) and M. J. Strauss et al, ibid., 35, 383 (1970).

The use of certain simple reductone compounds as silver halide developing agents has been disclosed, e.g., in U.S. Pat. Nos. 2,691,589; 3,615,440; 3,664,835; 3,672,896; 3,690,872; and 3,816,137.

It has now been discovered that catalytic hydrogenation of certain of the aforementioned bicyclic nitronate compounds in the presence of an acylating agent yields acylated reductone derivatives which upon acidic or alkaline hydrolysis give materials possessing pronounced reductone-like properties. In addition, it has been found that this new class of bicyclic compounds including both the acylated reductone derivatives and their hydrolysis products are useful as reducing agents and as photographic silver halide developing agents.

SUMMARY OF THE INVENTION

It is, therefore, one object of the present invention to provide a new class of bicyclic compounds including acylated bicyclic reductone derivatives and the hydrolysis products thereof.

Another object of the present invention is to provide a method of synthesizing the subject bicyclic compounds.

A further object of the present invention is to provide photographic products, processes and compositions employing the subject compounds for development of photosensitive silver halide materials.

Other objects of this invention will in part be obvious and will in part appear hereinafter.

The invention accordingly comprises the processes involving the several steps and the relation and order of one or more of such steps with respect to each of the others, and the products and compositions possessing the features, properties and relation of elements which are exemplified in the following detailed disclosure, and the scope of the application of which will be indicated in the claims.

DETAILED DESCRIPTION OF THE INVENTION

As noted above, it has been found that catalytic hydrogenation of certain bicyclic nitronate compounds in the presence of an acylating agent gives an acylated reductone derivative which undergoes hydrolysis in acid or base to yield compounds having typical reductone-like properties. The acylating agent employed should be stable to the conditions of the catalytic hydrogenation reaction and usually, is an acid anhydride. Because cyclic anhydrides, such as, benzoic anhydride render the reaction unnecessarily complex and often results in difficulty in isolating the acylated product, the anhydride employed preferably is derived from an aliphatic acid, particularly, a monocarboxylic alkanoic acid.

The novel bicyclic compounds of the present invention which comprise acylated bicyclic reductone derivatives and the hydrolysis products thereof may be represented by the formula

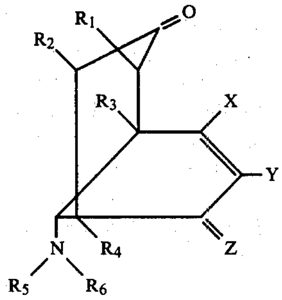

(I)

wherein $R_1$ and $R_2$, the same or different, each represents hydrogen, a hydrocarbon moiety, preferably an alkyl group, —COOH or —$COOR^1$ wherein $R^1$ is an alkyl group; $R_3$ and $R_4$, the same or different, each represent hydrogen or an alkyl group, $R_5$ represents hydrogen or —$COR^2$ wherein $R^2$ is an alkyl group; $R_6$ represents hydrogen when $R_5$ is hydrogen and represents hydrogen or —$OCOR^3$ wherein $R^3$ is an alkyl group the same as $R^2$ when $R_5$ represents —$COR^2$; X represents —OH, —$NH_2$ or —$NHCOR^4$ wherein $R^4$ represents an alkyl group the same as $R^2$; Y represents —OH or —$OCOR^5$ wherein $R^5$ represents an alkyl group the same as $R^2$; and Z represents O or $NCOR^6$ wherein $R^6$ is an alkyl group the same as $R^2$. Preferably, the alkyl groups comprising $R_1$, $R_2$, $R_3$ and $R_4$ and $R^1$, $R^2$, $R^3$, $R^4$, $R^5$ and $R^6$ are lower alkyl containing 1 to 6 carbon atoms. In a particularly preferred embodiment, $R_1$ and $R_2$ are the same and $R^3$ and $R^4$ are the same.

The novel bicyclic compounds of the present invention are prepared from certain bicyclic nitronate salts which may be represented by the formula

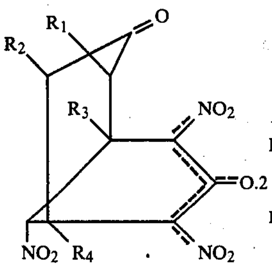

(II)

wherein $R_1$, $R_2$, $R_3$ and $R_4$ have the same meaning given in formula I above and $R_7$ and $R_8$ taken separately each represent alkyl groups containing 1 to 6 carbon atoms and taken together represent the atoms necessary to complete a saturated 5 or 6 member heterocyclic moiety derived from, e.g., morpholine, pyrrolidine, piperidine, piperazine and the like, and preferably piperidine.

The starting materials of formula II may be readily prepared by reacting an acyclic ketone, usually a ketone having a methylene group flanking the carbonyl group, e.g., acetone, with an aromatic polynitro compound, such as, picric acid, picramide or the like in the presence of a sec. aliphatic amine, such as, piperidine, morpholine or pyrrolidine to yield the bicyclic nitronate salt. See, for example, T. Kabeya et al, *Chem. Pharm. Bull.,* 1971, 19, p. 645, which discloses treating picric acid (wetted with about 15% water) with acetone in the presence of piperidine in a molar ratio of 1:30:2, respectively, to give the corresponding bicyclic nitronate salt.

In preparing the subject compounds, the bicyclic nitronate salts of formula II are reduced by hydrogenating a mixture of the selected bicyclic nitronate salt and an acid anhydride in the presence of a hydrogenation catalyst at ambient temperatures to give the corresponding acylated bicyclic reductones which may be represented by the formula

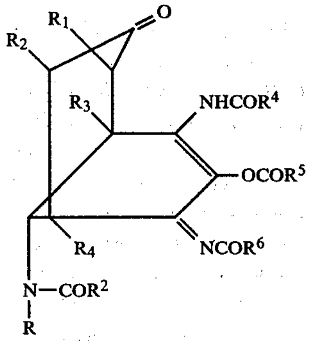

(III)

wherein R is hydrogen or $-OCOR^3$ and $R_1$, $R_2$, $R_3$, $R_4$, $R^2$, $R^3$, $R^4$, $R^5$ and $R^6$ have the same meaning given in formula I above.

As discussed above, the acid anhydride is preferably an alkanoic acid anhydride, $(R^2CO)_2O$ wherein $R^2$ is an alkyl group, particularly alkyl containing 1 to 6 carbon atoms. Useful anhydrides include acetic, caproic, propionic, valeric and butyric anhydrides. Preferably, acetic anhydride in admixture with acetic acid is employed. The amount of anhydride employed ranges between about 10 and 100 moles per mole of bicyclic nitronate salt. The hydrogenation catalyst may be any of those commonly employed in hydrogenation reactions, for example, a platinum, nickel or palladium catalyst, and for achieving increased yields, is preferably a palladium-on-carbon catalyst used in combination with a small amount of a zinc salt, for example, zinc acetate, to give between about 0.005 and 0.02 g of zinc per gram of catalyst. Ordinarily, the hydrogenation reaction is conducted at a temperature between about 20° and 40° C. and the hydrogen introduced at a pressure of between about 40 and 50 lbs. per square inch. The products are separated by treating with a solvent, e.g., hot acetone, in which one product is soluble and the other is not.

To prepare the hydrolysis products of the acylated bicyclic reductones, the compounds of formula III may be warmed in a 0.5 to 1.0 M aqueous solution of an alkali metal or alkaline earth metal hydroxide at 60° to 100° C. or refluxed with the aqueous hydroxide to give the alkaline hydrolysis product which may be represented by the formula

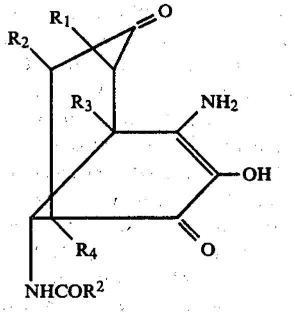

(IV)

wherein $R_1$, $R_2$, $R_3$, $R_4$ and $R^2$ have the same meaning given in formula I above.

The acylated reductone derivatives also may be hydrolyzed under acid conditions by refluxing the compounds of formula III in 2 N to 4 N aqueous hydrochloric acid to give the acid hydrolysis products which may be represented by the formula

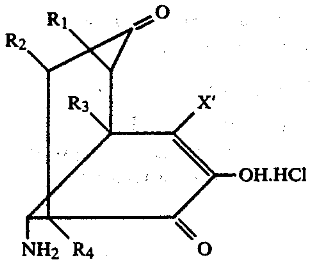

(V)

wherein X' is $-OH$ or $-NH_2$ and $R_1$, $R_2$, $R_3$ and $R_4$ have the same meaning given in formula I above. The products may be separated by fractional crystallization.

It will be appreciated that the hydrolysis reactions should be carried out in an inert atmosphere, e.g., under nitrogen and that the respective alkaline and acid solutions employed should be deaerated prior to use.

The above-described reaction sequence for synthesizing the subject compounds is illustrated below:

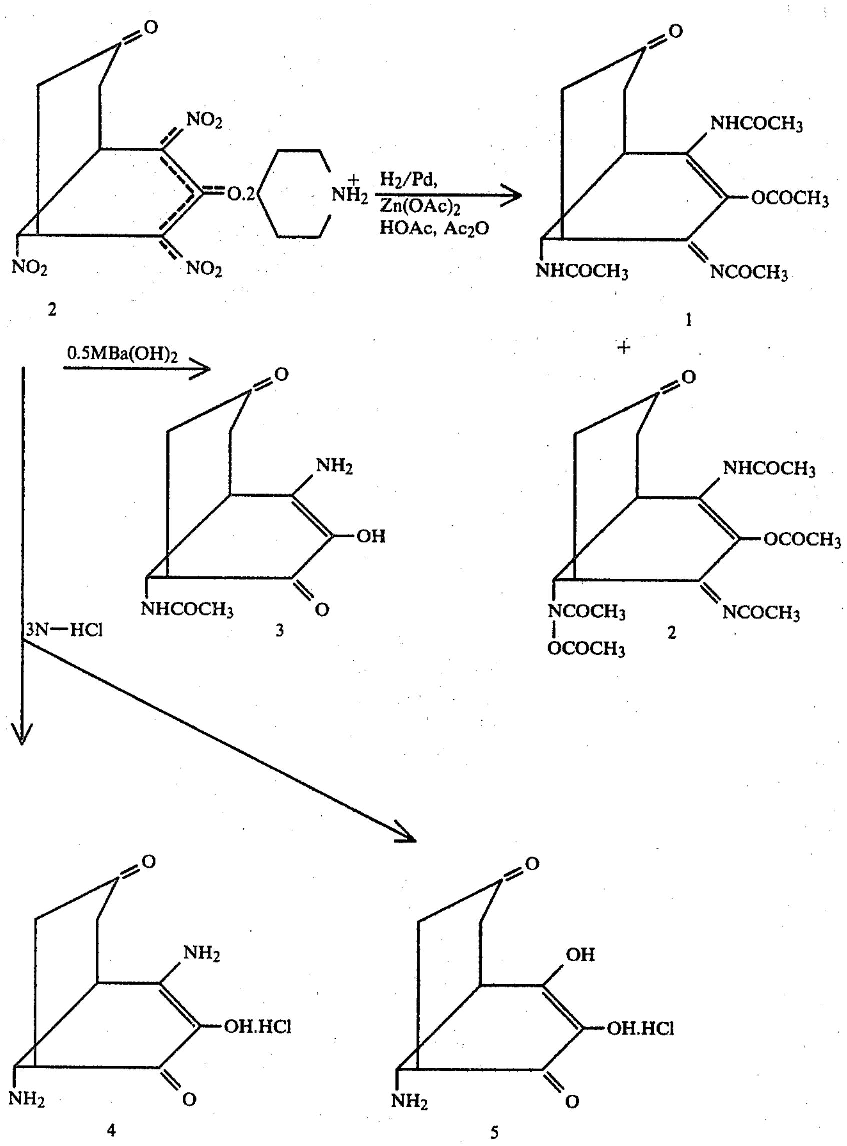
Specific examples of the novel bicyclic compounds of the present invention include:
(1)
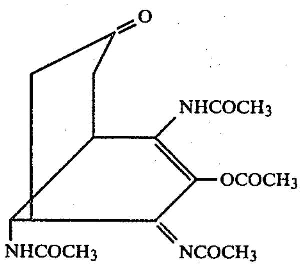
-continued
(2)
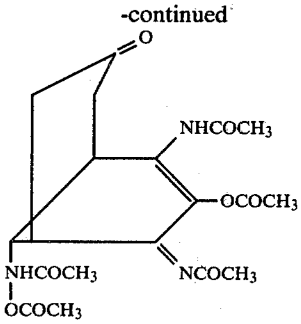

-continued

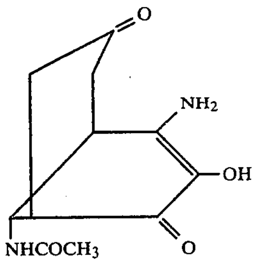

(3)

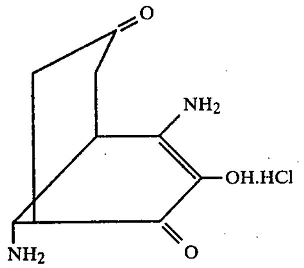

(4)

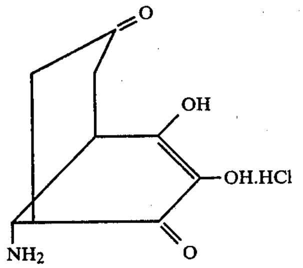

(5)

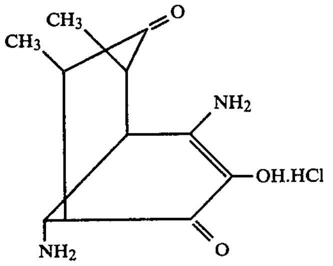

(6)

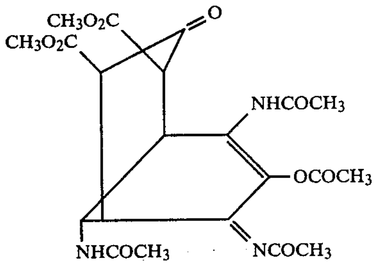

(7)

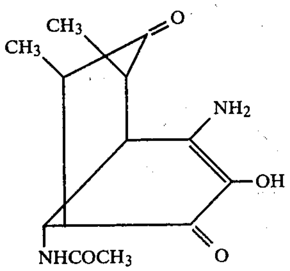

(8)

The following examples are given to further illustrate the present invention and are not intended to limit the scope thereof.

EXAMPLE 1

Preparation of 4,9-diacetamido-2-acetylimino-3-acetoxybicyclo[3,3,1]non-3-en-7-one:

4,9-Dinitro-3-hydroxy-7-oxobicyclo[3,3,1]non-2-ene-2-nitronic acid bis-piperidinium salt (162 g.; 0.314 mol) was combined with acetic acid (1 lt.), acetic anhydride (1 lt.), zinc acetate (0.60 g.) and 30% palladium/carbon catalyst (16.2 g.), and the mixture hydrogenated at a pressure of 50 lb. in$^{-2}$. After 1 hour, uptake of hydrogen was 3.0 mols. After removal of catalyst the mixture was taken to dryness at 45° C. in vacuo and the dark brown residue stirred with anhydrous ether (2 lt.) under nitrogen. After several hours a free-flowing solid was obtained. The solid was collected and dried immediately in vacuo giving the crude product (145 g.), which on recrystallization from acetonitrile (Norit) gave pure title compound as off-white irregular plates, m.p. 174°-176° C. (14.5 g.; 12.5%); νmax. 3370, 1770, 1710, 1663, 1620, 1512, and 1378 cm.$^{-1}$; λmax. ($CH_3CN$) 290 nm (ε21400); $^1$H nmr: $\delta_{Me_4Si(DMSO\text{-}d_6)}$ 1.83 (s, 3), 2.02 (s, 3), 2.07 (s, 3), 2.11 (s, 3), 2.46 (m, 2), 2.92 (m, 2), 3.11 (m, 1), 4.22 (m, 1), 4.41 (m, J=6$H_z$, 2.5$H_z$, 1), 8.06 (d, J=6$H_z$, 1), and 9.24 (s, 1); $^{13}$C nmr: $\delta_{Me_4Si}$ (DMSO-$d_6$) 205.4, 184.6, 169.7, 169.3, 167.6, 156.9, 141.2, 125.5, 49.9, 44.1, 43.6, 41.3, 35.5, 25.4, 24.5, 22.4, and 20.8 ppm.

Anal. Calcd. for $C_{17}H_{21}N_3O_6.\frac{1}{4}H_2O$: C, 55.50; H, 5.89; N, 11.42; O, 27.18. Found: C, 55.36; H, 6.05; N, 11.60; O, 26.94.

EXAMPLE 2

Preparation of 4-acetamido-9-(N-acetoxyacetamido)-2-acetylimino-3-acetoxybicyclo[3,3,1]non-3-en-7-one.

Cocentration of the mother-liquors from the recrystallization of Example 1 above gave a solid from which the compound of Example 1 could be extracted with hot acetone. Recrystallization of the acetone-insoluble material from hot acetonitrile then gave the title compound, m.p. 232°-233° C. (0.80 g.; 0.6% based on Example 1); νmax. 3380, 1808, 1780, 1720, 1620, and 1510 cm.$^{-1}$; λmax. 290 nm (ε21400); $^{13}$C nmr: $\delta_{Me_4Si}$ (DMSO-$d_6$) 204.7, 184.4, 170.3, 169.6, 168.3, 167.3, 156.7, 141.6, 125.8, 57.7, 44.4, 43.7, 40.2, 34.0, 25.1, 24.3, 20.6, 20.3, and 17.9 ppm.

Anal. Calcd. for $C_{19}H_{23}N_3O_8$: C, 54.15; H, 5.50; N, 9.97. Found C, 54.09, H, 5.71; N, 10.39.

EXAMPLE 3

Preparation of 9-acetamido-4-amino-3-hydroxybicyclo[3,3,1]non-3-en-2,7-dione.

The acetylimino compund prepared in Example 1 (1.1 g.; 0.003 mol.) was added to deaerated aqueous barium hydroxide solution (30 ml.; 0.5 M), and the mixture heated at 70°-80° C. in a stream of nitrogen for 3 hours. After cooling and removal of a small amount of insoluble material the solution, in an atmosphere of nitrogen, was titrated with 1 N-sulfuric acid to the phenol red end-point (ca. 12 ml. required). The resulting suspension was centrifuged and the clear supernatant evaporated at 30° C. in vacuo. The residue was recrystallized from water and the title compound collected as a white solid, m.p. >280° C. (0.10 g.; 14%); νmax. 3220, 3315, and 1718 cm.$^{-1}$; λmax. ($H_2O$) 315 nm (ε18400); $^{13}$C nmr: $\delta_{Me_4Si}$ (DMSO-$d_6$) 206.2, 184.1, 169.6, 146.7, 124.9, 51.1, 45.8, 44.6, 43.8, 38.7, and 22.3 ppm.

Anal. Calcd. for $C_{11}H_{14}N_2O_4.\frac{1}{4}H_2O$: C, 54.43; H, 6.02; N, 11.54. Found: C, 54.4, H, 5.7; N, 11.2.

EXAMPLE 4

Preparation of 4,9-diamino-3-hydroxybicyclo[3,3,1]-non-3-en-2,7-dione hydrochloride.

The acetylimino compound prepared in Example 1 (5.0 g.; 0.0136 mol.) was added to deaerated 3 N-hydrochloric acid (135 ml.) and the mixture heated under reflux in a stream of nitrogen for 4 hours. Evaporation at 40° C. in vacuo gave a beige solid which was purified by fractional crystallization from a mixture of methanol and ethyl acetate to give the title compound as an off-white solid, m.p. >300° C. (1.06 g.; 36%); $\nu$max. 3350, 3235, 1725, 1715, 1610, and 1420 cm.$^{-1}$; $\lambda$max. (MeOH) 320 nm ($\epsilon$18400); $^{13}C$ nmr: $\delta_{Me4Si}$ ($D_2O$) 209.8, 184.4, 153.9, 125.4, 53.0, 45.4, 45.0, 44.0, and 39.1 ppm.

Anal. Calcd. for $C_9H_{12}N_2O_3HCl$: C, 46.46; H, 5.63; Cl, 15.24; N, 12.04. Found: C, 45.9; H, 5.8; Cl, 15.2; N, 11.9.

EXAMPLE 5

Preparation of 9-amino-3,4-dihydroxybicyclo[3,3,1]-non-3-en-2,7-dione hydrochloride.

The acetylimino compound prepared in Example 1 (5.0 g.; 0.0136 mol.) was added to deaerated 3 N-hydrochloric acid (135 ml.) and the mixture heated under reflux in a stream of nitrogen for 4 hours, then cooled and taken to dryness at 40° C. in vacuo. The resulting solid was treated with hot methanol, and the undissolved material collected and recrystallized from water (Norit) giving the title compound as a white solid, m.p. >300° C. (0.80 g.; 23.5%); $\nu$max. 3400, 1703, 1620, and 1490 cm.$^{-1}$; $^{13}C$ nmr: $\delta_{Me4Si}$ ($D_2O$) 209.8, 174.9, 130.9, 52.9, 44.0, and 42.9 ppm.

Anal. Calcd. for $C_9H_{11}NO_4.HCl.H_2O$: C, 42.95; H, 5.61; Cl, 14.09; N, 5.57. Found: C, 43.2; H, 5.6; Cl, 14.15; N, 5.3.

The 4,9-dinitro-3-hydroxy-7-oxobicyclo[3,3,1]non-2-ene-2-nitronic acid bispiperidinium salt used in Example 1 was prepared as follows:

Picric acid (51.00 g.; 0.20 mols.; containing about 10% of water) was dissolved in acetone (500 ml.), and piperidine (40 ml.; 0.40 mols.) added cautiously. There was a mild exotherm. The mixture was allowed to stand for 5 days, after which the solid was collected, washed sparingly with acetone, and dried immediately in vacuo, giving the nitronate salt acetone solvate as golden yellow needles, m.p. 115.5°-116.5° C. (37.38 g.; 36.3%); $\nu$max. 1713, 1542, and 1320 cm.$^{-1}$; $\lambda$max. (0.1 N-NaOH) 237 ($\epsilon$18800) and 400 nm ($\epsilon$23200); $^1H$ nmr: $\delta_{Me4Si}$ (DMSO-$d_6$) 1.52 (m, 12); 2.07 (s, 6), 2.40 (m, 2), 2.83 (m, 10), 4.34 (m, 2), 5.59 (t, J=3$H_z$, 1), and 8.36 (s, 4); $^{13}C$ nmr: $\delta_{Me4Si}$ (1 M-KOH) 215.2, 214.4, 173.2, 122.7, 121.2, 45.4, 44.1, 37.7, 30.5, 24.1, and 23.0 ppm.

Anal. Calcd. for $C_{19}H_{31}N_5O_8.C_3H_6O$: C, 51.25; H, 7.23; N, 13.59; O, 27.93. Found: C, 51.29; H, 7.15; N, 13.72; O, 28.00.

It will be appreciated that other compounds within the scope of the present invention may be prepared according to the foregoing procedures.

As indicated above, the novel bicyclic compounds of the present invention are useful as reducing agents and as photographic silver halide developing agents in conventional or "tray" development and in diffusion transfer processes for forming positive transfer images in silver or in color. Such diffusion transfer processes are now well known in the art; see, for example, U.S. Pat. Nos. 2,543,181; 2,647,056; 2,983,606; 3,719,489, etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image.

In silver diffusion transfer processes, processing of the exposed silver halide emulsion is effected in the presence of a photographic silver halide solvent, such as sodium thiosulfate or uracil, which forms a diffusible complex with the undeveloped silver halide. The soluble silver complex thus formed diffuses to the superposed image-receiving layer where the transferred silver ions are deposited as metallic silver to provide the silver transfer image.

In preparing silver prints in this manner, the image-receiving layer preferably includes certain materials, the presence of which, during the transfer process has a desirable effect on the amount and character of silver precipitated on the image-receiving element. Materials of this type are specifically described in U.S. Pat. Nos. 2,690,237 and 2,698,245, both issued in the name of Edwin H. Land on Dec. 28, 1954 and U.S. Pat. No. 3,671,241 of Edwin H. Land issued on June 20, 1972.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

Separating the photosensitive element from the image-receiving layer may be controlled so that the layer of processing composition is removed from the image-receiving layer or the layer of processing composition is caused to remain in contact with the image-receiving layer, e.g., to provide it with a protective coating. Techniques which enable such results to be accomplished as desired are described in U.S. Pat. No. 2,647,054 issued to Edwin H. Land on July 28, 1953. In general, the processing reagents are selected so that traces remaining after the solidified processing layer has been separated from the silver image or which remain in said layer adhered as a protective coating on the silver image are colorless or pale, so as not to appreciably affect the appearance of the image and to have little or no tendency to adversely react with the silver image.

The developing agents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488 of Edwin H. Land and 3,615,428 of Lucretia J. Weed and in 3,894,871 of Edwin H. Land issued July 15, 1975.

The subject developing agents also may be employed in diffusion transfer processes where the final image is in dye, and as appropriate for the particular color process, the developing agent may be used as the principal developer, for example, in the processes of aforementioned U.S. Pat. No. 3,719,489 or as an auxiliary developer, for example, in the processes of aforementioned U.S. Pat. No. 2,983,606. In these diffusion transfer processes, a photosensitive component comprising at least one photosensitive silver halide emulsion having a dye image-providing compound associated therewith in the same or an in adjacent layer is exposed to form a developable image then developed with a processing composition to form an imagewise distribution of a soluble and diffusible image-providing material which is transferred, at least in part, by diffusion, to a superposed image-receiving component comprising at least a dyeable stratum. These processes rely for color image formation upon a differential in mobility or solubility of dye image-providing material obtained as a function of development so as to provide an imagewise distribution of such material which is more diffusible and which, therefore, may be selectively transferred to the superposed dyeable stratum. The differential in mobility or solubility may be obtained, for example, by a chemical action such as a redox reaction, a silver ion-associated cleavage reaction or a coupling reaction.

The dye image-providing materials which may be employed in such processes generally may be characterized as either (1) initially soluble or diffusible in the processing composition but which are selectively rendered non-diffusible in an imagewise pattern as a function of development; or (2) initially insoluble or non-diffusible in the processing composition but which are selectively rendered diffusible in an imagewise pattern as a function of development. These materials may be complete dyes or dye intermediates, e.g., color couplers.

Examples of initially soluble or diffusible materials and their use in color diffusion transfer processes are disclosed, for example, in U.S. Pat. Nos. 3,087,817; 2,661,293; 2,693,244; 2,698,798; 2,802,735; and 2,983,606. Examples of initially non-diffusible materials and their use in color transfer systems are disclosed in U.S. Pat. Nos. 3,443,939; 3,443,940; 3,227,550; 3,227,551; 3,227,552; 3,227,554; 3,243,294; 3,445,228; 3,719,488 and 3,719,489.

In any of these systems, multicolor images may be obtained by employing a photosensitive element containing at least two selectively sensitized silver halide layers each having associated therewith a dye image-providing material exhibiting the desired spectral absorption characteristics. The most commonly employed elements of this type are the so-called tripack structures employing a blue-, a green- and a red-sensitive silver halide layer having associated therewith, respectively, a yellow, a magenta and a cyan image-providing material.

The photosensitive and image-receiving elements may be separate components which are brought together during processing and thereafter retained together as the final print or separated following image formation; or they may together comprise a unitary structure, e.g., an integral negative-positive film structure wherein the negative and positive, i.e., the photosensitive element and image-receiving element are laminated and/or otherwise physically retained together at least prior to image formation. Integral negative-positive film structures adapted for forming color transfer images viewable without separation, i.e., wherein the image-receiving component containing the dye transfer image need not be separated from the photosensitive component for viewing purposes are described and claimed in U.S. Pat. Nos. 3,415,644; 3,415,645; 3,415,646; 3,573,043 and 3,573,044 in the name of Edwin H. Land and in 3,594,164 and 3,594,165 in the name of Howard G. Rogers.

In conventional development and in diffusion transfer photographic processes, the subject compounds may be used as the sole silver halide developing agent, or they may be employed in combination with another silver halide developing agent as an auxiliary developer or as the main component of the developing combination. Examples of developing agents that may be used in combination with the subject compounds include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as, catechol, 4-phenyl catechol and tertiary butyl catechol; aminophenols, such as 2,4,6-triaminophenol, 2,4-diaminophenol dihydrochloride and 4,6-diamino-ortho-cresol; 1,4-diaminobenzenes, such as, p-phenylenediamine, 1,2,4-triaminobenzene and 4-amino-2-methyl-N,N-diethylaniline; ascorbic acid and its derivatives, such as, ascorbic acid, isoascorbic acid and 5,6-isopropylidine ascorbic acid; and hydroxylamines, such as N,N-di-(2-ethoxyethyl) hydroxylamine and N,N-di(2-methoxyethoxyethyl) hydroxylamine.

When the compounds of the present invention are used in diffusion transfer processes, the processing composition if it is to be applied to the emulsion by being spread thereon in a thin layer, usually includes a film-forming thickening agent. The processing composition may comprise, for example, one or more developing agents of the present invention and optionally, one or more conventional developing agents such as those enumerated above, an alkali such as sodium hydroxide or potassium hydroxide and a viscosity-increasing agent such as a high molecular weight polymer, e.g., sodium carboxymethyl cellulose, hydroxyethyl cellulose, or carboxymethyl hydroxyethyl cellulose. As noted above, in the production of silver transfer image, a silver halide solvent is employed which may be included in the processing composition, or if desired, a silver halide solvent precursor such as those disclosed in U.S. Pat. No. 3,698,898 of J. Michael Grasshoff and Lloyd D. Taylor may be disposed in a layer of the film unit. In addition to the above ingredients, the processing composition may be further modified by the inclusion of restrainers, preservatives and other components commonly employed in developer compositions. All these materials are preferably in aqueous solution.

Rather than being dissolved in the aqueous alkaline processing composition prior to application thereof to an exposed silver halide emulsion, the developing agents of the present invention may be disposed prior to exposure in the photosensitive element, e.g., by placing them in, on or behind a silver halide emulsion layer. In this instance, the processing composition containing the developing agent is formed by application to the photosensitive element of an aqueous alkaline solution capable of solubilizing the developing agent. In diffusion transfer processes, the subject developing agents usually are contained in the processing composition. Whether the developing agent is initially disposed in the processing composition or in the photosensitive element, upon application of the processing composition, the developing agent is provided for processing the photoexposed silver halide material.

To illustrate the utility of the above-defined compounds as photographic developing agents, a photosensitive silver iodobromide emulsion on a support was exposed to a step wedge and processed by spreading a layer of processing composition approximately 1.2 mils. thick between the exposed emulsion and a superposed image-receiving element comprising a layer of regenerated cellulose containing colloidal palladium sulfide carried on a transparent support. The processing composition was prepared by adding a developing agent of the present invention in a concentration of 5% by weight (except where noted) to the following formulation:

| | |
|---|---|
| Water | 814.0 g. |
| Potassium hydroxide (Aqueous 50% w/w solution) | 348.0 g. |
| Hydroxyethyl cellulose | 35.0 g. |
| Zinc acetate | 15.0 g. |
| Triethanolamine | 5.6 g. |
| Uracil | 50.0 g. |

After an imbibition period of approximately one minute, the developed silver halide emulsion was separated from the image-receiving element, and the maximum and minimum transmission densities were measured for the positive image.

The foregoing procedure was repeated using the same photosensitive element, a Polaroid Land Type 107 image-receiving element and a processing composition that was the same as above except that sodium hydroxide (348.0 g.—aqueous 50% w/w solution) was substituted for potassium hydroxide and sodium thiosulfate ("hypo"—50.0 g.) was substituted for uracil. Developing agents of the present invention were added to the processing composition in a concentration of 5% by weight. The photosensitive element was exposed and processed in the same manner described above and after an imbibition period of about one minute, the photosensitive and image-receiving elements were separated and the maximum and minimum reflection densities were measured for the positive image.

The compounds added as developing agents to the processing composition containing uracil as the photographic silver halide solvent (Test A) and added to the processing composition containing hypo as the photographic silver halide solvent (Test B), and the respective transmission and reflection density measurements for the positive images obtained with each of the compounds are set forth in the following Table.

TABLE

| Compound (Example No.) | Test A Trans. Density $D_{max}/D_{min}$ | Test B Reflection Density $D_{max}/D_{min}$ |
|---|---|---|
| 1 | -*- | 0.9/0.5 |
| 3** | 0.8/0.5 | -***- |
| 4 | 2.5/0.2 | -***- |
| 5 | -****- | 1.2/0.6 |

*non-discriminated positive image
**3% by weight concentration
***not tested
****weak but discriminated positive image and fixed negative It will be apparent from the above that compounds of the present invention may be selected for use with a given silver halide solvent to achieve the desired balancing of development and silver halide complexing rates to provide a positive silver transfer image. In this regard, it will be appreciated that the relative proportions of the subject developing agents and the choice and relative proportion of the other ingredients of the processing compositions may be varied to suit the requirements of a given photographic system. Also, it is within the scope of this invention to modify the formulations set forth above by the substitution of alkalies, antifoggants and so forth other than those specifically mentioned. Where desirable, it is also contemplated to include in the processing composition, other components as commonly used in the photographic art.

As mentioned above, rather than being dissolved in the aqueous alkaline processing composition prior to application thereof to an exposed silver halide emulsion, it is also contemplated that the developing agents of the present invention may be disposed prior to exposure in a layer or layers of the photographic film unit, e.g., by placing them in or behind a silver halide emulsion layer in the photosensitive element. In this instance, the processing composition containing the developing agents is formed by application to the photosensitive element of an aqueous alkaline solution capable of solubilizing the developing agent.

Since certain changes may be made in the above compositions and processes without departing from the scope of the invention herein involved, it is intended that all matter contained in the above description should be interpreted as illustrative and not in a limiting sense.

We claim:

1. A compound of the formula

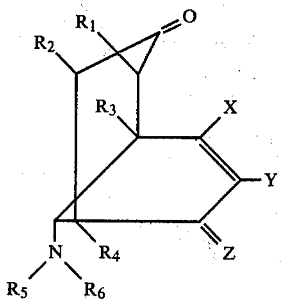

wherein $R_1$ and $R_2$, the same or different, each represent hydrogen, an alkyl group, —COOH or —$COOR^1$ wherein $R^1$ is an alkyl group; $R_3$ and $R_4$, the same or different, each represent hydrogen or an alkyl group, $R_5$ represents hydrogen or —$COR^2$ wherein $R^2$ is an alkyl group containing 1-6 carbon atoms; $R_6$ represents hydrogen when $R_5$ is hydrogen and represents hydrogen or —$OCOR^3$ wherein $R^3$ is an alkyl group the same as $R^2$ when $R_5$ represents —$COR^2$ provided that when $R_6$ is —$OCOR^3$, Y is —$OCOR^5$; X represents —OH or —$NH_2$ when Y is —OH or X represents —$NHCOR^4$ wherein $R^4$ represents an alkyl group the same as $R^2$ when Y is —$OCOR^5$; Y represents —OH or —$OCOR^5$ wherein $R^5$ represents an alkyl group the same as $R^2$; and Z represents O when Y is —OH or $NCOR^6$ wherein $R^6$ is an alkyl group the same as $R^2$ when Y is —$OCOR^5$.

2. A compound as defined in claim 1 wherein said $R_1$ and $R_2$ are the same.

3. A compound as defined in claim 2 wherein said $R_1$ and $R_2$ are hydrogen.

4. A compound as defined in claim 1 wherein $R_3$ and $R_4$ are the same.

5. A compound as defined in claim 4 wherein $R_3$ and $R_4$ are hydrogen.

6. A compound as defined in claim 1 wherein said $R_5$ represents —$COR^2$ and said $R_6$ represents hydrogen.

7. A compound as defined in claim 1 wherein said $R_5$ and $R_6$ each represent hydrogen.

8. The compound

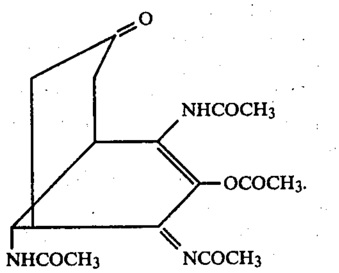

9. The compound

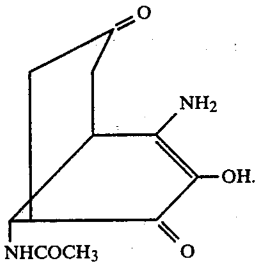

10. The compound

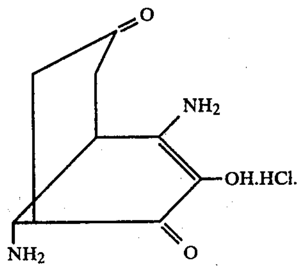

11. The compound

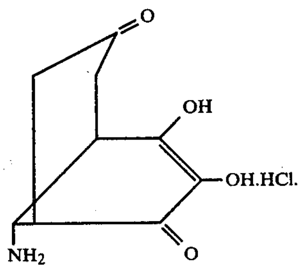

12. A process of preparing certain bicyclic compounds which comprises hydrogenating a mixture of (a) a bicyclic nitronate salt of the formula

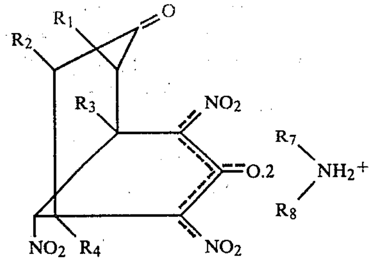

wherein $R_1$ and $R_2$, the same or different, each represent hydrogen, an alkyl group, —COOH or —$COOR^1$ wherein $R^1$ is an alkyl group; $R_3$ and $R_4$, the same or different, each represent hydrogen or an alkyl group; and $R_7$ and $R_8$ taken separately each represent alkyl groups containing 1 to 6 carbon atoms and taken together represent the atoms necessary to complete a saturated 5 or 6 member heterocyclic moiety and (b) an anhydride of a monocarboxylic alkanoic acid by introducing hydrogen at a pressure of between about 40 and 50 lbs per square inch in the presence of a hydrogenation catalyst at ambient temperature to yield (c) the corresponding acylated bicyclic compound of the formula

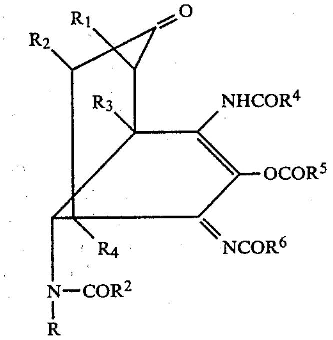

wherein $R^2$ is an alkyl group containing 1-6 carbon atoms; R is hydrogen or —$OCOR^3$ wherein $R^3$ is an alkyl group the same as $R^2$; $R^4$, $R^5$ and $R^6$ each are alkyl groups the same as $R^2$; and $R_1$, $R_2$, $R_3$ and $R_4$ have the same meaning given above.

13. A process as defined in claim 12 wherein said catalyst is palladium-on-carbon in combination with a zinc salt.

14. A process as defined in claim 12 which includes the additional step of hydrolyzing said acylated bicyclic compound (c) wherein R represents hydrogen by refluxing with an aqueous solution of hydroxide to yield (d) the alkaline hydrolysis product of the formula

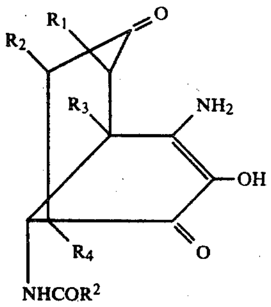

wherein $R_1$ and $R_2$ are hydrogen, alkyl or —COOH and $R_3$, $R_4$ and $R^2$ have the same meaning given above.

15. A process as defined in claim 12 which includes the additional step of hydrolyzing said acylated bicyclic compound (c) wherein said R is hydrogen by refluxing in 2 N to 4 N aqueous hydrochloric acid to give the acid hydrolysis product of the formula

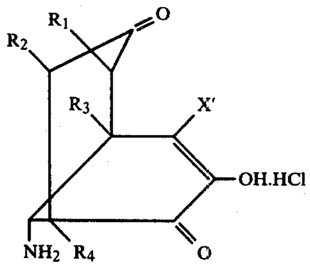

wherein X' is —OH or —$NH_2$, $R_1$ and $R_2$ are hydrogen, alkyl or —COOH and $R_3$ and $R_4$ have the same meaning given above.

* * * * *